United States Patent [19]

Skarlos et al.

[11] 4,390,957
[45] Jun. 28, 1983

[54] COAL SLURRY MONITOR MEANS AND METHOD

[75] Inventors: Leonidas Skarlos, Beaumont; Roger M. Dille, Port Arthur, both of Tex.

[73] Assignee: Texaco Inc., White Plains, N.Y.

[21] Appl. No.: 190,121

[22] Filed: Sep. 24, 1980

[51] Int. Cl.³ .............................................. G01N 27/46
[52] U.S. Cl. .................................... 364/550; 324/300; 73/61.1 R; 364/502
[58] Field of Search ............... 364/550, 497, 496, 500, 364/501, 502; 324/300, 306, 307; 356/410; 73/73, 61.1 R; 422/62, 68; 23/230 A

[56] References Cited

U.S. PATENT DOCUMENTS

| | | | |
|---|---|---|---|
| 3,691,455 | 9/1972 | Moisio et al. | 324/307 |
| 3,771,271 | 2/1973 | Goetchius et al. | 73/61.1 R X |
| 3,909,598 | 9/1975 | Collins et al. | 364/497 X |
| 3,925,721 | 12/1975 | Petroff | 324/300 |
| 3,950,137 | 4/1976 | Larson et al. | 422/68 X |
| 3,966,973 | 6/1976 | Henry et al. | 324/307 X |
| 4,048,854 | 9/1977 | Herzl | 364/509 X |
| 4,141,645 | 2/1979 | Reid et al. | 364/550 X |
| 4,256,695 | 3/1981 | Gillespie | 364/500 X |
| 4,271,474 | 6/1981 | Belanger et al. | 364/500 |
| 4,311,488 | 1/1982 | Verschuur | 364/502 X |

*Primary Examiner*—Edward J. Wise
*Attorney, Agent, or Firm*—Carl G. Ries; Robert A. Kulason; Ronald G. Gillespie

[57] ABSTRACT

A monitor receives a slurry of coal and water and provides an output signal corresponding to the coal content of the slurry. The monitor includes sensing apparatus which senses the hydrogen content of the water in the slurry and provides a corresponding signal. A circuit supplies a signal corresponding to the hydrogen content of water. An output network provides the output signal corresponding to the coal content of the slurry in accordance with the signals from the sensing apparatus and the circuit.

8 Claims, 3 Drawing Figures ns and method"

COAL SLURRY MONITOR MEANS AND METHOD

BACKGROUND OF THE INVENTION

1. Field of the Invention

The present invention relates to monitoring in general and, more particularly, to monitors for monitoring slurries.

SUMMARY OF THE INVENTION

A monitor receives a slurry of coal and water and provides an output signal corresponding to the coal content of the slurry. The monitor includes sensing apparatus which senses the hydrogen content of the water in the slurry and provides a corresponding signal. A circuit provides a signal corresponding to the hydrogen content of water. An output network provides the output signal corresponding to the coal content of the slurry in accordance with the signals from the sensing apparatus and the circuit.

The object and advantages of the invention will appear more fully hereinafter, from a consideration of the detailed description which follows, taken together with the accompanying drawings wherein one embodiment is illustrated by way of example. It is to be expressly understood, however, that the drawings are for illustrative purposes only and are not to be construed as defining the limits of the invention.

DESCRIPTION OF THE INVENTION

Figure 1:
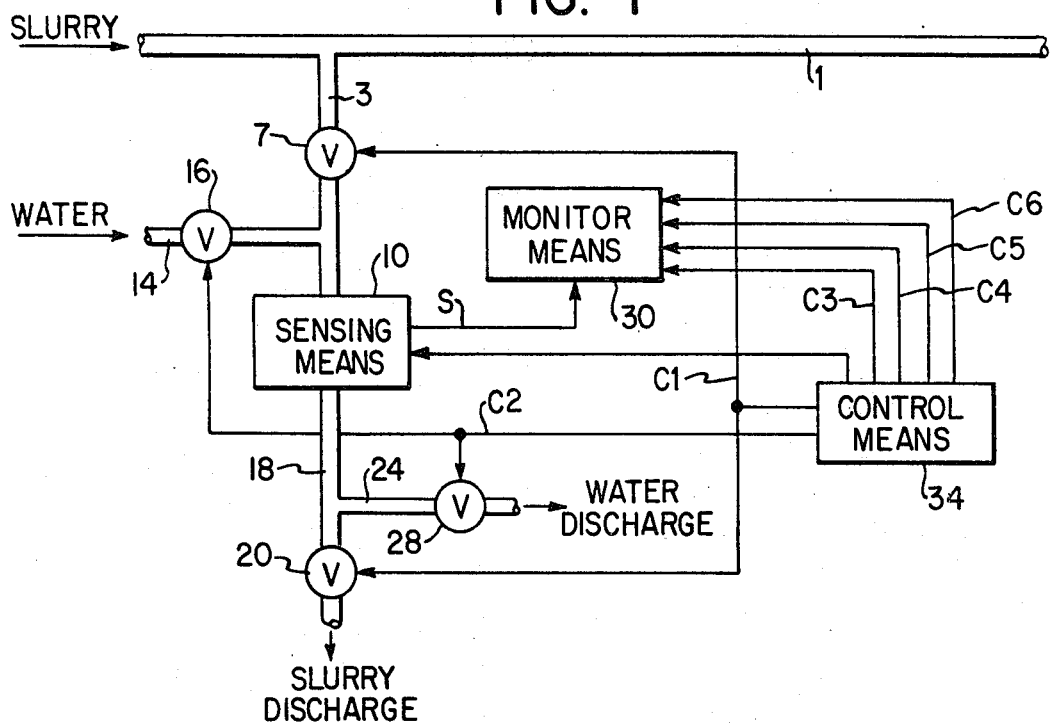
FIG. 1 is a simplified block diagram of a coal slurry monitor constructed in accordance with the present invention.

A mixture of coal and water, hereinafter called slurry, flows through a line 1. A portion of the slurry is drawn off through a line 3, having a valve 7, and is provided to sensing means 10. Water is provided through a line 14 having a valve 16 to flow into pipe 3 to sensing means 10. Sensing means 10 utilizes low resolution nuclear magnetic resonance techniques in sensing properties of either the slurry or the water and provides a signal S corresponding to percent of hydrogen in the water in the sample.

Hydrogen associated with liquids, such as water, can be sensed by low resolution nuclear magnetic resonance, whereas hydrogen in solids, such as coal, is not. The water in line 14 should come from the same source as the water used in preparing the slurry, especially if the water contains significant quantities of soluble hydrogen containing materials, such as ammonia or formaltis. Sensing means 10 may have a Newport analyzer Mark III, manufactured by Newport Oxford Industries, or an equivalent. The slurry is discharged through a line 18 having a valve 20. The water is discharged through line 18 and through another line 24 having a valve 28.

Sensing means 10 provides signal S to monitor means 30. Control means 34 provides control signal C1 to valves 7, 20 and a control signal C2 to valves 16, 28 to control the fluid flow through sensing means 10 as hereinafter explained. Control means 34 also provides control signals C3 through C6 to monitor means 30.

The operation of the system as such is that with valves 7 and 20 in the open position, slurry passes through sensing means 10 which provides a signal corresponding to the hydrogen content of the water in the slurry. During calibration, valves 7 and 20 are initially closed and then valves 16 and 28 are opened so that water flows through sensing means 10 so that signal S now corresponds to the hydrogen content of the water.

Monitor means 30 utilizes the following equations $$W = (Ss/Sw)100\%, \quad 1.$$

where Ss is the signal from sensing means 10 for a unit volume of slurry, Sw is the signal for a unit volume of water and W is the percent weight water in the slurry.

$$C = 100 - W, \quad 2.$$

where C is the percent weight of the coal in the slurry.

Figure 2:
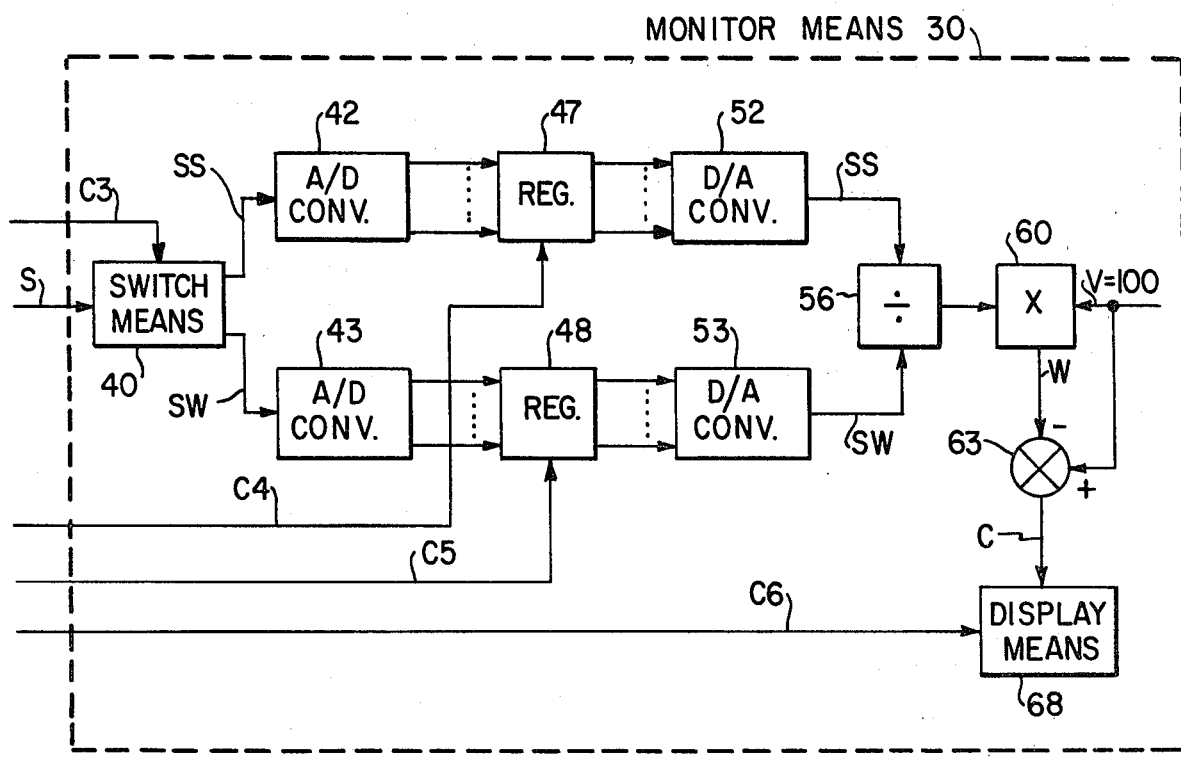
FIGS. 2 and 3 are detailed block diagrams of the monitor means and the control means, respectively, shown in FIG. 1.

Referring now to FIG. 2, switch means 40 receives signal S and control signal C3. Switching means 40 is in essence an electronic single-pole double throw switch which in effect takes signal S and provides it at one of its two outputs. When signal C3 is at a low logic level, switch means 40 provides signal S as signal ss, corresponding to the instantaneous hydrogen content of the water in the slurry. When signal C3 is at a high logic level, switch means 40 provides signal S as signal sw corresponding to the hydrogen content of the water in the sample.

Signals ss and sw are provided to analog-to-digital converters 42 and 43, respectively, which in turn provide corresponding digital signals to registers 47 and 48. Registers 47 and 48 are controlled by control signals C4 and C5, respectively, to enter the digital signals and provide digital signals to digital-to-analog converters 52 and 53, respectively, which provide signal Ss and Sw, respectively. Signals Ss and Sw correspond to the sampled percent weight of the slurry and the water, respectively. A divider 56 divides signal Ss with signals Sw to provide a signal corresponding to the sensed weight of water to a multiplier 60. Multiplier 60 multiplies the signal with a direct current voltage corresponding to a value of 100 to provide a signal corresponding to the term W in equation 1.

Subtracting means 63 subtracts signal W from the voltage corresponding to 100 to provide a signal C corresponding to the term C in equation 2. Signal C is provided to display means 68. Display means 68 can either visually display signal C in the form of a numeric display or record an analog trace of signal C, or both. Display means 68 is inhibited by control signal C6 as hereinafter explained so that when switching from a measuring mode of operation to a calibration mode and back transient data can be omitted.

Figure 3:
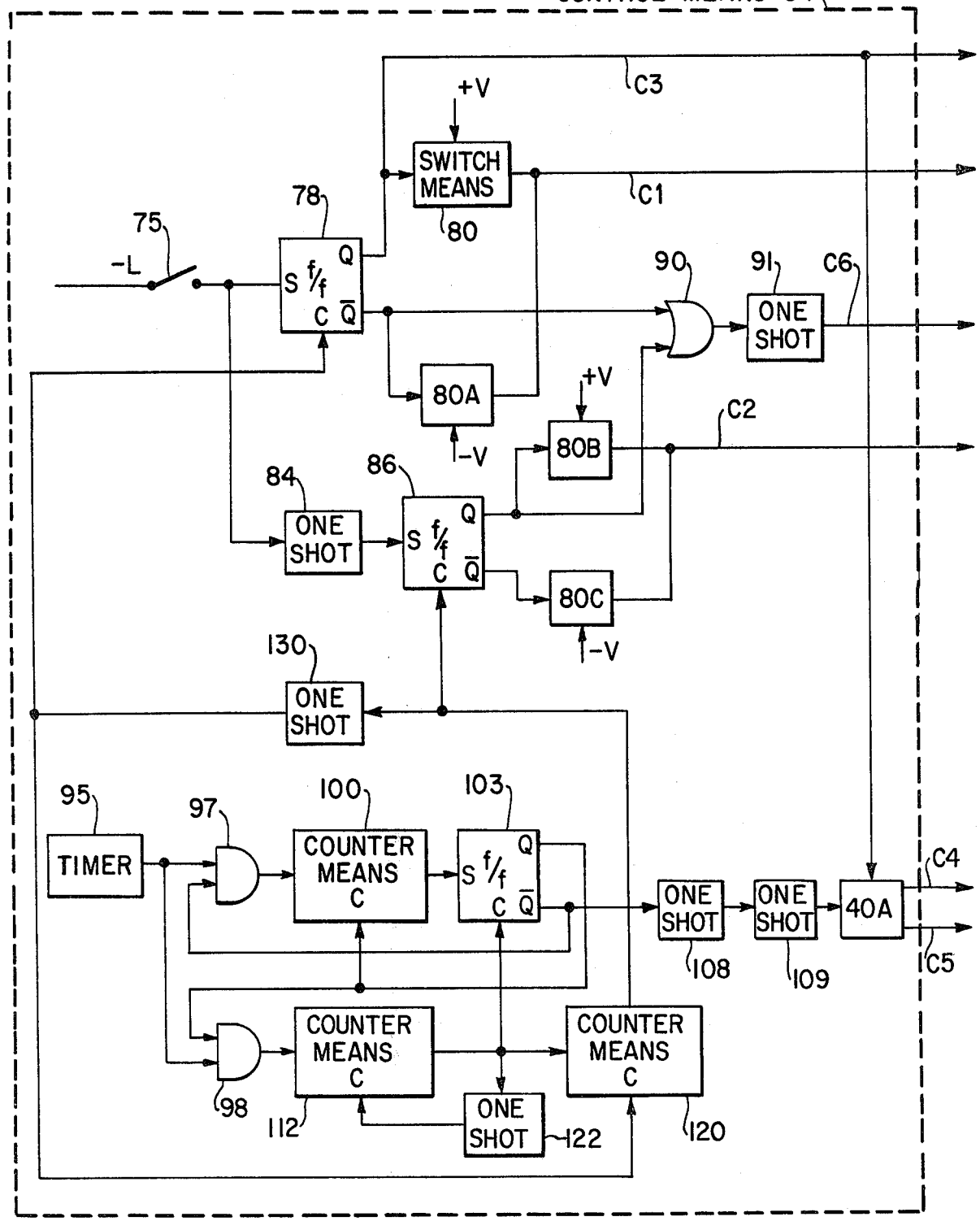

Referring now to FIG. 3, control means 34 includes a manually operative switch 75 receiving a negative logic voltage L so that when momentarily activated, switch 75 provides a negative pulse to the set input of a flip-flop 78. Flip-flop 78 has a Q and $\overline{Q}$ output connected to switch means 80 and 80A, respectively, whose outputs are commonly connected. The signal appearing at the Q output of flip-flop 78 is control signal C3. Switch means 80 receives a positive direct current voltage +V and is rendered conductive by a high logic level signal appearing at the Q output of flip-flop 78 to pass voltage +V as control signal C1 and is rendered non-conductive by a low logic level signal appearing at the Q output to block voltage +V. Elements having a numeric designation with a suffix are similar to elements having the same numeric designation without a suffix.

Switch means 80A receives a negative direct current voltage −V and is controlled by a high logic level signal appearing at the $\bar{Q}$ output of flip-flop 78 to pass voltage −V as signal C1 and to block voltage −V when the signal appearing at the $\bar{Q}$ output of flip-flop 78 is at a low logic level.

The negative pulse from the operation of switch 75 also triggers a one-shot multivibrator 84 to provide a pulse which in turn is applied to the set input of a flip-flop 86 triggering it to the set state. Flip-flop 86 has its Q output connected to switch means 80B, which receives voltage −V, and its $\bar{Q}$ ouput connected to switch means 80C which receives voltage +V. Switch means 80B and 80C are connected in the same manner as switch means 80 and 80A so that combined they provide signal C2.

The $\bar{Q}$ output of flip-flop 78 and the Q output of flip-flop 86 are provided to an OR gate 90 whose output is connected to another one-shot multivibrator 91. One-shot 91 provides control signal C6.

A timer 95 provides timing pulses to AND gates 97, 98. AND gate 97 provides pulses, when enabled, to counting means 100 which count the pulses until a predetermined number is reached and then provides a pulse to the set input of a flip-flop 103. The Q output of flip-flop 103 is connected to AND gate 98 and to the clear input of counter means 100. The $\bar{Q}$ output of flip-flop 103 is connected to AND gate 97 and to a one-shot multivibrator 108.

One-shot 108 is connected to another one-shot multivibrator which in turn is connected to switch means 40A. Switch means 40A also receives control signal C3, and selects pulses from one-shot 109 to be provided as control signal C4 or as control signal C5. The output of AND gate 98 is provided to counter means 112 which provides a pulse output when it counts a predetermined number of passed pulses from AND gate 98. Counter means 112 provides the pulse to another counter means 120, to another one-shot multivibrator 122 and to the clear input of flip-flop 103. One-shot 122 provides pulses to the clear input of counter means 112.

Counter means 120 counts the pulses provided by counter means 112 and upon reaching a predetermined count provides a pulse to a one-shot multivibrator 130 and to the clear input of flipf-flop 86. One-shot 130 provides a pulse, in response to being triggered, to the clear inputs of flip-flop 78 and of counter means 120.

In operation, flip-flop 78 is in a clear state and provides a low logic level signal as signal C3 which causes signal S from sensing means 10 to be provided as signal ss. Because flip-flop 78 is in the clear state, switch means 80A passes voltage −V as control signal C1 which keeps valves 7 and 20 open and flip-flop 86 is in the clear state which provides voltage +V as signal C2 thereby maintaining valves 16 and 28 closed so that sensing means 10 has slurry flowing through it.

Initially flip-flop 103 is in a clear state, thereby causing AND gate 97 to pass timing pulses from timer 95 to counter means 100. Upon reaching a predetermined count, counter means 100 provides a pulse to flip-flop 103 triggering it to the set state so that it provides a high logic level signal which enables AND gate 98 so that it passes timing pulses to counter means 112 for counting.

It should be noted that the predetermined count of counter means 112 corresponds to the test duration.

Upon reaching the predetermined count, counter means 112 provides a pulse to one-shot 122 and to counter 120 which is counted by counter means 120. One-shot 122, in response to the pulse from counter 112, provides a clear pulse to the C input of counter 112. The pulse from counter means 112 also clears flip-flop 103 so that the signal at $\bar{Q}$ output goes to a high logic level and again enables AND gate 97 while the signal at the Q output goes to a low logic level, thereby disabling AND gate 98 so that the test procedure starts over again.

The signal at the $\bar{Q}$ output of flip-flop 103 in going to a low logic level triggers one-shot 108 which in turn provides a time delay pulse. The pulse from one-shot 108 triggers another one-shot multivibrator 109 to provide a pulse which passes through switch means 40A and is provided as enter pulse C4 to register 47. Register 47 enters the data from analog to digital converter 42 in response to the enter pulse. The time delay pulse from one-shot 108 ensures that the signal S from sensing means 10 has stabilized before entering the corresponding digital signals into either register 47 or register 48.

To calibrate the herebefore described monitor, an operator depresses switch 75 triggering flip-flop 78 to a set state. At this time, the signal C3 at the Q output of flip-flop 78 goes to a high logic level, causing switch means 40 to provide signal S as signal SW and to cause switch means 40A to provide a pulse from one-shot 109 as enter pulse C5. Further, switch means 80 is rendered conductive to provide signal C1 as a positive direct current voltage, causing valves 7 and 20 to close.

One-shot 84 is also activated by the pulse from switch 75 and acts as a time delay in providing a pulse to flip-flop 86, causing it to go to a set state. While in the set state, switches 80B and 80C are rendered conductive and non conductive, respectively, so as to provide −V as control signal C2 thereby opening valves 16 and 28 at some time interval after the closure of valves 7 and 20.

Again, timer 95, AND gates 97 and 98, counter means 100, 112, flip-flop 103 and one-shot 122 cooperate as hereinbefore described. However, now counter means 120 is providing a count of the measurement being made during calibration and upon reaching a predetermined count, it provides a pulse output to one-shot 130 and to the clear input of flip-flop 86. Clearing flip-flop 86 causes switches 80B and 80C to provide +V as signal C2 thereby closing valves 16 and 28. One-shot 130 provides a pulse to the clear input of flip-flop 78 causing it to change to a clear state thereby causing switch means 80 and 80A to provide voltage −V as signal C1 thereby opening valves 7 and 20 at some time interval after the closing of valves 16 and 28.

Again, during the calibration procedures, the pulses provided by one-shot 109 were provided as enter pulses C5 to register 48 to let it enter the signals corresponding to SW.

The changing of either the $\bar{Q}$ output signal from flip-flop 78 or the Q output signal from flip-flop 86 causes OR gate 90 to go to a low logic level triggering one-shot multivibrator 91 which provides an inhibiting pulse C6. C6 inhibits display means 68 for a certain time period during the changing of the operation of sensing means 10 from test procedure to calibration procedure.

The present invention as hereinbefore described is a monitor for monitoring the coal content of a slurry of coal and water.

What is claimed is:

1. A monitor receiving a slurry of coal and water for providing an output signal corresponding to the weight by percent of the coal in the slurry comprising sensing means for sensing the hydrogen content of the water in the slurry and providing a corresponding signal, said sensing means utilizing low resolution nuclear magnetic resonance in its sensing, water signal means for providing a signal corresponding to the hydrogen content of water, output means connected to the sensing means and to the water signal means for providing the output signal corresponding to the coal content of the slurry in accordance with the signals from the sensing means and the water signal means, and source means for providing water through the sensing means in accordance with a first control signal, valve means receiving the slurry for providing the slurry through the sensing means in accordance with a second control signal; and in which the output means includes control signal means for providing the first and second control signals to the source means and to the valve means so that the sensing means will provide its signal corresponding either to the water or to the slurry depending on whether the slurry or the water is passing.

2. A monitor as described in claim 1 in which the output means also includes first switch means having two outputs connected to the sensing means and to the control means and responsive to a third control signal for providing the signal from the sensing means at one output when the signal from the sensing means corresponds to the hydrogen content of the water in the slurry and at the other output where the signal from the sensing means corresponds to the hydrogen content of the water, first and second sample and holds means connected to the one output and to the other output, respectively, of the first switch means and to the control signal means for being controlled by the fourth and fifth control signals, respectively, from the control signal means to sample and store the signals appearing at the outputs of the first switch means to provide corresponding signals, dividing means connected to the first and second sample and hold means for dividing the signal from the second sample and hold means into the signal from the first sample and hold means to provide a signal corresponding to the weight of water in the slurry, and means connected to the dividing means for providing the output signal corresponding to the weight by percent of coal in the slurry.

3. A monitor as described in claim 2 in which the control signal means includes first control network means receiving a negative direct current voltage for providing the first, second and third control signals, timer means for providing clock pulses, and second control network means connected to the timer means, to the first control network means and to the first and second sample and hold means for providing the fourth and fifth control signals to the first and second sample and hold means, respectively, and a clearing pulse to the first control network means.

4. A monitor as described in claim 3 in which the first control network means includes a manually operative switch receiving the negative voltage, first flip-flop means having a set input connected to the switch, a clear input connected to the second control network means and Q and $\bar{Q}$ outputs for providing a high logic level signal at its Q output as the third control signal and a low logic level at its $\bar{Q}$ output while in a set state and a low logic level signal and a high logic level signal at its Q and $\bar{Q}$ outputs, respectively, and responsive to operation of the switch to be triggered to the set state and responsive to a pulse applied to the clear input to be triggered to a clear state, second switch means connected to the Q and $\bar{Q}$ outputs of the first flip-flop means and receiving a positive direct current voltage V and a negative direct current voltage $-V$ for being controlled by the signals appearing at the Q and $\bar{Q}$ outputs of the first flip-flop means to select one of the two voltages to be provided as the second control signal, a first one-shot means connected to the switch and responsive to operation of the switch to provide a pulse, second flip-flop means having a set input connected to the first one-shot means, a clear input connected to the second control network means and Q and $\bar{Q}$ outputs for being triggered to the set state by a pulse from the first one-shot means and to a clear state by a pulse from the second control network means, and third switch means connected to the Q and $\bar{Q}$ outputs of the second flip-flop means and receiving the voltages $+V$ and $-V$ for selecting one of the direct current voltages, in accordance with the signals appearing at the Q and $\bar{Q}$ outputs of the second flip-flop means, to be provided as the first control signal.

5. A monitor as described in claim 4 in which the second control network means includes first and second AND gates connected to the timer means for controlling passage of the clock pulses, first and second counter means connected to the first and second AND gates, respectively, and having clear inputs and inputs for counting the pulses passed by the first and second AND gates, respectively, and providing pulses when they reach predetermined counts, third flip-flop means having its set input connected to the first counter means, a clear input connected to the second counter means, a Q output connected to the clear input of the first counter means and to be second AND gate and a $\bar{Q}$ output connected to the first AND gate for providing signals to control the passage of clock pulses by the first and second AND gates and for clearing the first counter means, second one-shot means connected to the Q output of the third flip-flop means and responsive to the change of the signal appearing at the Q output from a high logic level to a low logic level for providing a pulse, third one-shot means connected to the second one-shot means for providing a pulse in response to a pulse being provided by the second one-shot means, fourth switch means connected to the Q output of the first flip-flop means and to the third one-shot means and responsive to the signal appearing at the Q output of the first flip-flop means for providing the pulses from the third one-shot means as either the fourth control signal or the fifth control signal, third counter means connected to the clear input of the second flip-flop means, the second counter means and having a clear input for counting pulses provided by the second counter means and for providing a pulse after reaching a third predetermined count to the second flip-flop means, so as to trigger the second flip-flop means to a clear state, fourth one-shot means connected to the third counter means, and to the clear inputs of the first flip-flop means and the third counter means and responsive to a pulse from the third counter means for providing a clear pulse whereby the first flip-flop means is triggered to the clear state and the third counter means is cleared, and fifth one-shot means connected to the clear input of the second counter means and responsive to a pulse from the second counter means for clearing the second counter means.

6. A method of monitoring a slurry of coal and water to determine the coal content of the slurry which comprises the steps of:
- providing water from a source to sensing apparatus in accordance with a first control signal,
- providing the slurry to the sensing apparatus in accordance with a second control signal,
- providing the first and second control signals to the sensing apparatus in a manner so that either water or the slurry, but not both, is provided to the sensing apparatus,
- sensing the hydrogen content of the slurry when the slurry is provided to the sensing apparatus,
- sensing the hydrogen content of the water when the water is provided to the sensing apparatus, and
- determining the coal content of the slurry in accordance with the sensed hydrogen content of the slurry and the determined hydrogen content of the water.

7. A method as described in claim 6 in which the hydrogen content of the slurry is sensed utilizing low resolution nuclear magnetic resonance.

8. A method as described in claim 7 in which the water hydrogen determination includes sensing the hydrogen content of the water utilizing low resolution nuclear magnetic resonance.

* * * * *

UNITED STATES PATENT AND TRADEMARK OFFICE
CERTIFICATE OF CORRECTION

PATENT NO. : 4,390,957
DATED : June 28, 1983
INVENTOR(S) : Leonidas Skarlos & Roger M. Dille It is certified that error appears in the above—identified patent and that said Letters Patent is hereby corrected as shown below:

Column 5, line 62  "Q and Q" should read --Q and $\bar{Q}$--;

Column 5, line 64,  "Q" should read --$\bar{Q}$--;

Column 5, line 66,  "Q and Q" should read --Q and $\bar{Q}$--;

Column 6, line 5,  "Q and Q" should read --Q and $\bar{Q}$--;

Column 6, line 12,  "Q and Q" should read --Q and $\bar{Q}$--;

Column 6, line 16,  "Q and Q" should read --Q and $\bar{Q}$--;

Column 6, line 35,  "Q" should read --$\bar{Q}$--;
line 39,  "Q" should read --$\bar{Q}$--;
line 41,  "Q" should read --$\bar{Q}$--;

Signed and Sealed this

Fourth Day of October 1983

[SEAL]

Attest:

GERALD J. MOSSINGHOFF

Attesting Officer    Commissioner of Patents and Trademarks